(12) United States Patent
Laster

(10) Patent No.: US 12,030,922 B2
(45) Date of Patent: Jul. 9, 2024

(54) IL-31 IMPROVES EFFICACY OF MACROPHAGE-BASED ADOPTIVE CELL THERAPY FOR CANCER

(71) Applicant: OncoHost Ltd., Binyamina (IL)

(72) Inventor: Morris C. Laster, Jerusalem (IL)

(73) Assignee: OncoHost Ltd., Binyamina (IL)

( * ) Notice: Subject to any disclaimer, the term of this patent is extended or adjusted under 35 U.S.C. 154(b) by 1389 days.

(21) Appl. No.: 16/516,286

(22) Filed: Jul. 19, 2019

(65) Prior Publication Data
US 2020/0062816 A1 Feb. 27, 2020

Related U.S. Application Data

(60) Provisional application No. 62/700,507, filed on Jul. 19, 2018.

(51) Int. Cl.
| | |
|---|---|
| *A61K 35/15* | (2015.01) |
| *A61P 35/00* | (2006.01) |
| *C07K 14/54* | (2006.01) |
| *C07K 14/705* | (2006.01) |
| *C07K 14/725* | (2006.01) |
| *C07K 14/735* | (2006.01) |
| *C07K 16/28* | (2006.01) |
| *C07K 16/32* | (2006.01) |
| *C12N 5/0786* | (2010.01) |
| *A61K 38/00* | (2006.01) |

(52) U.S. Cl.
CPC ............. *C07K 14/54* (2013.01); *A61K 35/15* (2013.01); *A61P 35/00* (2018.01); *C07K 14/7051* (2013.01); *C07K 14/70517* (2013.01); *C07K 14/70521* (2013.01); *C07K 14/70535* (2013.01); *C07K 14/7056* (2013.01); *C07K 16/2803* (2013.01); *C07K 16/32* (2013.01); *C12N 5/0645* (2013.01); *A61K 38/00* (2013.01); *C07K 2317/622* (2013.01); *C07K 2319/03* (2013.01); *C07K 2319/30* (2013.01); *C07K 2319/33* (2013.01)

(58) Field of Classification Search
None
See application file for complete search history.

(56) References Cited

U.S. PATENT DOCUMENTS

| 2017/0072019 A1 | 3/2017 | Fremder |
| 2017/0016657 A1 | 6/2017 | O'Neill et al. |

FOREIGN PATENT DOCUMENTS

| WO | 2015173812 A1 | 11/2015 |
| WO | 2017019848 A1 | 2/2017 |

OTHER PUBLICATIONS

Nardin et al., "Macrophages and Cancer" Frontiers in Bioscience 13, 3494-3505, May 1, 2008. doi: 10.2741/2944. PMID: 18508451.
Andreesen, et al., "Adoptive transfer of tumor cytotoxic macrophages generated in vitro from circulating blood monocytes: a new approach to cancer immunotherapy". Cancer Res. 50(23): 7450-7456 (1990).
Beatty, et al., "Chimeric antigen receptor-modified T cells for the treatment of solid tumors: Defining the challenges and next steps". Pharmacol. Ther. 166:30-39. (2016).
Corneilissen, et al., "Ultraviolet B radiation and reactive oxygen species modulate interleukin-31 expression in T lymphocytes, monocytes and dendritic cells". Br. J. Dermatol. 165(5): 966-975 (2011).
Dambacher, et al.,. "Interleukin 31 mediates MAP kinase and STAT1/3 activation in intestinal epithelial cells and its expression is upregulated in inflammatory bowel disease." Gut 56: 1257-1265 (2007).
Davidi, et al., "The antiangiogenic role of the pro-inflammatory cytokine interleukin-31". Oncotarget 8: 16430-16444 (2017).
Dillon, et al., "Interleukin 31, a cytokine produced by activated T cells, induces dermatitis in mice". Nat. Immunol. 5: 752-760 (2004).
Feretti, et al., "The interleukin (IL)-31/IL-31R axis contributes to tumor growth in human follicular lymphoma." eukemia 29: 958-967 (2015).
Fidler, "Inhibition of pulmonary metastasis by intravenous injection of specifically activated macrophages". Cancer Res. 34: 1074-1078. (1974).
Fridman, et al., "The immune contexture in human tumours: impact on clinical outcome." Nat. Rev. Cancer 12(4): 298-306 (2012).
Harrer, et al., "Chimeric Antigen Receptors in Different Cell Types: New Vehicles Join the Race". Hum. Gene Ther. 29: 547-558 (2018).
Hermanns, "Oncostatin M and interleukin-31: Cytokines, receptors, signal transduction and physiology". Cytokine Growth Factor Rev. 26: 545-558 (2015).
Houot. et al., "T-cell-based Immunotherapy: Adoptive Cell Transfer and Checkpoint Inhibition". Cancer Immunol. Res. 3(10): 1115-1122 (2015).
Huang, et al., "Interleukin-armed chimeric antigen receptor-modified T cells for cancer immunotherapy". Gene Ther. 25: 192-197 (2017).
Jackson, et al., "Driving CAR T-cells forward". Nat. Rev. Clin. Oncol. 13(6): 370-383 (2016).
Lee, et al., "Macrophage-based cell therapies: The long and winding road". J. Control Release 240: 527-540 (2016).
Lei, et al., "SCF and IL-31 rather than IL-17 and BAFF are potential indicators in patients with allergic asthma". Allergy 63: 327-332 (2008).
Mantvani, et al., "Tumor-associated macrophages as a paradigm of macrophage plasticity, diversity, and polarization: lessons and open questions". Arterioscler. Thromb. Vasc. Biol. 33: 1478-1483 (2013).
Maude, et al., "Chimeric antigen receptor T cells for sustained remissions in leukemia". N. Engl. J. Med. 371(16): 1507-1517 (2014).
Neis, et al., "Enhanced expression levels of IL-31 correlate with IL-4 and IL-13 in atopic and allergic contact dermatitis". J. Allergy Clin. Immunol. 118: 930-937 (2006).

(Continued)

*Primary Examiner* — Michael D Burkhart
(74) *Attorney, Agent, or Firm* — The Roy Gross Law Firm, LLC; Roy Gross

(57) ABSTRACT

The present invention provides macrophages genetically modified to express IL-31 or both IL-31 and a chimeric antigen receptor (CAR) for treatment of cancer. It further provides methods for treatment of cancer comprising administration of IL-31 along with genetically unmodified macrophages or genetically modified to express a CAR.

15 Claims, 3 Drawing Sheets

Specification includes a Sequence Listing.

(56) References Cited

OTHER PUBLICATIONS

Niyonsaba, et al., "Antimicrobial peptides human beta-defensins and cathelicidin LL-37 induce the secretion of a pruritogenic cytokine IL-31 by human mast cells". J. Immunol. 184(7): 3526-3534 (2010).

Ohmattsu, et al., "Serum IL-31 levels are increased in patients with cutaneous T-cell lymphoma". Acta Derm. Venereol. 92: 282-283 (2012).

Rosenberg, et al., "Durable complete responses in heavily pretreated patients with metastatic melanoma using T-cell transfer immunotherapy. Clinical cancer research : an official journal of the American Association for Cancer" Research 17(13): 4550-4557 (2011).

Wang, et al., "Immunotherapy of a murine lymphoma by adoptive transfer of syngeneic macrophages activated with bisantrene". Cancer Res. 46: 503-506 (1986).

Zeng, et al., "Clinical Significance of Serum Interleukin-31 and Interleukin-33 Levels in Patients of Endometrial Cancer: A Case Control Study". Dis. Markers 9262919. (2016).

WIPO International Search for PCT/IL2019/050810, pp. 6, dated Oct. 22, 2019.

SEQUENCE LISTING

```
<160> NUMBER OF SEQ ID NOS: 8

<210> SEQ ID NO 1
<211> LENGTH: 164
<212> TYPE: PRT
<213> ORGANISM: Homo sapiens

<400> SEQUENCE: 1

Met Ala Ser His Ser Gly Pro Ser Thr Ser Val Leu Phe Leu Phe Cys
1               5                   10                  15

Cys Leu Gly Gly Trp Leu Ala Ser His Thr Leu Pro Val Arg Leu Leu
            20                  25                  30

Arg Pro Ser Asp Asp Val Gln Lys Ile Val Glu Glu Leu Gln Ser Leu
        35                  40                  45

Ser Lys Met Leu Leu Lys Asp Val Glu Glu Lys Gly Val Leu Val
    50                  55                  60

Ser Gln Asn Tyr Thr Leu Pro Cys Leu Ser Pro Asp Ala Gln Pro Pro
65                  70                  75                  80

Asn Asn Ile His Ser Pro Ala Ile Arg Ala Tyr Leu Lys Thr Ile Arg
                85                  90                  95

Gln Leu Asp Asn Lys Ser Val Ile Asp Glu Ile Ile Glu His Leu Asp
            100                 105                 110
```

```
Lys Leu Ile Phe Gln Asp Ala Pro Glu Thr Asn Ile Ser Val Pro Thr
            115                 120                 125

Asp Thr His Glu Cys Lys Arg Phe Ile Leu Thr Ile Ser Gln Gln Phe
130                 135                 140

Ser Glu Cys Met Asp Leu Ala Leu Lys Ser Leu Thr Ser Gly Ala Gln
145                 150                 155                 160

Gln Ala Thr Thr

<210> SEQ ID NO 2
<211> LENGTH: 442
<212> TYPE: DNA
<213> ORGANISM: Homo sapiens

<400> SEQUENCE: 2
atggcctctc actcaggccc ctcgacgtct gtgctctttc tgttctgctg cctgggaggc      60
tggctggcct cccacacgtt gcccgtccgt ttactacgac caagtggaaa gatgtggagg     120
aagagaaggg cgtgctcgtg tcccagaatt acacgctgcc gtgtctcagc cctgacgccc     180
agccgccaaa caacatccac agcccagcca tccgggcata tctcaagaca atcagacagc     240
tagacaacaa atctgttatt gatgagatca tagagcacct cgacaaactc atatttcaag     300
atgcaccaga acaaacatt tctgtgccaa cagacaccca tgaatgtaaa cgcttcatcc     360
tgactatttc tcaacagttt tcagagtgca tggacctcgc actaaaatca ttgacctctg     420
gagcccaaca ggccaccact ta                                              442

<210> SEQ ID NO 3
<211> LENGTH: 22
<212> TYPE: DNA
<213> ORGANISM: Artificial Sequence
<220> FEATURE:
<223> OTHER INFORMATION: ARG1 oligonucleotide sequence

<400> SEQUENCE: 3
ctccaagcca aagtccttag ag                                               22

<210> SEQ ID NO 4
<211> LENGTH: 22
<212> TYPE: DNA
<213> ORGANISM: Artificial Sequence
<220> FEATURE:
<223> OTHER INFORMATION: ARG1 oligonucleotide sequence

<400> SEQUENCE: 4
aggagctgtc attagggaca tc                                               22

<210> SEQ ID NO 5
<211> LENGTH: 23
<212> TYPE: DNA
<213> ORGANISM: Artificial Sequence
<220> FEATURE:
<223> OTHER INFORMATION: iNOS oligonucleotide sequence

<400> SEQUENCE: 5
gttctcagcc caacaataca aga                                              23

<210> SEQ ID NO 6
<211> LENGTH: 19
<212> TYPE: DNA
<213> ORGANISM: Artificial Sequence
<220> FEATURE:
<223> OTHER INFORMATION: iNOS oligonucleotide sequence
```

```
<400> SEQUENCE: 6
gtggacgggt cgatgtcac                                              19

<210> SEQ ID NO 7
<211> LENGTH: 22
<212> TYPE: DNA
<213> ORGANISM: Artificial Sequence
<220> FEATURE:
<223> OTHER INFORMATION: Hsp90 oligonucleotide sequence

<400> SEQUENCE: 7
tcgtcagagc tgatgatgaa gt                                          22

<210> SEQ ID NO 8
<211> LENGTH: 23
<212> TYPE: DNA
<213> ORGANISM: Artificial Sequence
<220> FEATURE:
<223> OTHER INFORMATION: Hsp90 oligonucleotide sequence

<400> SEQUENCE: 8
gcgtttaacc catccaactg aat                                         23
```

IL-31 IMPROVES EFFICACY OF MACROPHAGE-BASED ADOPTIVE CELL THERAPY FOR CANCER

CROSS REFERENCE

The present application claims priority and the filing date of U.S. Provisional Application No. 62/700,507, filed Jul. 19, 2018, the entire contents being hereby incorporated by reference in its entirety as if fully disclosed herein.

REFERENCE TO SEQUENCE LISTING

Submitted as part of this patent application is a Sequence Listing filed as an ASCII text file named UEONC1-0006US-SeqList-ONCO-006US.txt having a file size of 4,000 bytes and generated on Jul. 19, 2019, the content of which is hereby expressly incorporated by reference in its entirety.

FIELD OF THE INVENTION

The present invention relates in general to the field of cancer therapy and, in particular, for treatment of cancer by adoptive cell-transfer (ACT) immunotherapy.

BACKGROUND OF THE INVENTION

Cancer immunotherapy involves the use of components of the immune system to treat cancer, for example, by artificial stimulation of the immune system, improving on the immune system's natural ability to fight cancer.

Adoptive cell-transfer therapy (ACT) represents a promising type of cancer immunotherapy that exploits the inherent ability of the immune system to eradicate tumor cells. In ACT, immune cells are extracted from patient tumor samples or peripheral blood, expanded ex vivo, and then reinfused into the patient. These immune cells are either naturally capable of eradicating tumor cells or have been reprogrammed to do so by genetic modification or treatment with specific cytokines.

T lymphocytes play a critical role in immunosurveillance and tumor cell eradication. They express receptors that recognize tumor-associated antigens and, once activated, exert direct cytotoxic effects against malignant cells. In the clinic, the presence of tumor-infiltrating T lymphocytes (TILs) is associated with favorable prognosis in patients with various tumor types (Fridman et al., 2012).

TIL therapy represents the first type of ACT therapy to be developed and involves the extraction, selection and ex vivo expansion of naturally-occurring lymphocytes isolated from resected tumors. The expanded TILs, which express T cell receptors with high avidity for tumor antigens, are then infused back into the body. In TIL therapy, patients are typically lymphodepleted to eliminate suppressor cells such as T-regulatory cells and myeloid-derived suppressor cells. Patients also receive high-dose of IL-2, a T cell growth factor that promotes in vivo expansion of the transferred TILs (Houot et al., 2015). TIL therapy has been proven successful in advanced metastatic melanoma (Rosenberg et al., 2011). However, it has several limitations: for example, it requires surgical resection of the tumor. In addition, it is not suitable for tumors lacking immune infiltrate, or in which antigen processing and presentation is downregulated.

Two novel approaches, both of which are based on the ex vivo genetic engineering of peripheral T cells, have been developed to overcome such obstacles. In the first approach, peripheral T cells are engineered to express a T cell receptor (TCR) with specificity against a tumor antigen. Such T cells recognize processed peptide antigens expressed in the context of MHC.

The most prominent type of ACT to date involves autologous T cells that have been reprogrammed to target tumor cells via the expression of a chimeric antigen receptor (CAR). CAR-T therapy has demonstrated dramatic successes in a number of clinical trials, most notably for hematological malignancies, and has been approved by the FDA for certain types of cancers (Harrer et al., 2018; Jackson et al., 2016). In this second approach, T cells are engineered to express a chimeric antigen receptor (CAR) comprising an extracellular single-chain variable fragment (scFv) and an intracellular signaling domain. The extracellular portion of the CAR allows the recognition of a specific tumor antigen, and the intracellular signaling domain stimulates T-cell activation. CAR-T cells do not depend on antigen processing and presentation as they recognize cell surface antigens in a non-MHC-restricted manner. While first-generation CARs include the intracellular signaling domain of CD3, second- and third-generation CARs also include the intracellular domains of one or multiple costimulatory molecules, such as CD28, OX40, and 4-1BB to improve persistence and proliferation of infused T cells (Houot et al., 2015). CAR-T therapy directed against CD19 has demonstrated dramatic success for acute lymphoblastic leukemia (ALL) where complete remission was achieved in 90% of patients (Maude et al., 2014). However, despite the promising responses demonstrated in hematological malignancies, the efficacy of CAR-T therapy in solid tumors is limited. Possible explanations for this include immunosuppression in the hostile tumor microenvironment and poor homing and infiltrating capabilities of CAR-T cells (Beatty et al., 2016). Conceivably, immunomodulatory cytokines can be used to overcome such obstacles, thereby enhancing the anti-tumor efficacy of CAR-T therapy. Indeed, several preclinical studies have demonstrated that further modifying CAR-T cells to secrete the pro-inflammatory cytokine IL-12 offers protection from the inhibitory tumor microenvironment and improves anti-tumor efficacy. In addition, systemic co-administration of cytokines such as IL-2, IL-7, IL-12 or IL-15 has demonstrated potential in improving efficacy of CAR-T therapy in various preclinical and clinical studies (reviewed in Huang et al., 2017).

Macrophages are one of the most abundant immune cell types in the tumor microenvironment. Endogenous tumor-associated macrophages (TAM) can either promote or suppress tumor progression, depending on their activation state. In early tumors, 'classically activated' macrophages have an inflammatory, tumoricidal phenotype. Such macrophages are also known as anti-tumor macrophages or M1-like macrophages. However, in established tumors, macrophages polarize toward an 'alternatively activated' phenotype, with angiogenic, anti-inflammatory and immunosuppressive properties. These macrophages are also known as pro-tumor or M2-like macrophages (Mantovani and Locati, 2013). Accordingly, adoptive transfer of anti-tumor macrophages has been explored as a therapeutic strategy for cancer. Preclinical studies have shown that the administration of activated macrophages significantly decreases tumor growth and metastasis in various murine tumor models (Fidler, 1974; Wang et al., 1986). However, to date, clinical trials were unsuccessful in achieving therapeutic goals (Lee et al., 2016). One of the major obstacles in macrophage-based ACT is loss of the ex vivo-induced anti-tumor phenotype once the macrophages encounter signals produced within the tumor microenvironment. Thus, a need exists in the art for more effective compositions and methods to maintain adoptively transferred macrophages in the desired functional state.

IL-31 is an immunoregulatory cytokine belonging to the IL-6 cytokine family. It is predominantly expressed by activated CD4+ T cells of a Th2 phenotype, as well as mast cells, monocytes, macrophages and dendritic cells (Dillon et al., 2004; Cornelissen et al., 2011; Niyonsaba et al., 2910). IL-31 signals through a heterodimeric complex consisting of the ubiquitously expressed oncostatin M receptor β (OSMRβ) and the IL-31 receptor α (IL-31RA), which has a more restricted expression pattern (Hermanns, 2015). An initial study demonstrated that transgenic mice overexpressing IL-31 or wildtype mice administered with IL-31 develop atopic-dermatitis-like symptoms consistent with a T cell-mediated pro-inflammatory role in the skin (Dillon et al., 2004). In humans, high levels of IL-31 are strongly associated with allergic conditions such as atopic dermatitis (Neis et al., 2006), inflammatory bowel disease (Dambacher et al., 2007) and asthma (Lei et al., 2008).

The role of IL-31 in cancer is not well-characterized. There are only a few published studies, suggesting either pro- or anti-tumorigenic effects. For example, clinical studies link IL-31 to hematological malignancies such as cutaneous T cell lymphoma and follicular B cell lymphoma (Ferretti et al., 2015; Ohmatsu et al., 2012). In addition, elevated IL-31 and IL-33 levels correlate with poor prognosis in endometrial cancer patients (Zeng et al., 2016). Recently, IL-31 was shown to treat angiogenesis-related disorders including cancer and to reduce or prevent metastasis (WO 2015/173812; Davidi et al., 2017).

SUMMARY OF THE INVENTION

Macrophages residing in the tumor microenvironment (TME) are known as tumor-associated macrophages (TAM). They are highly plastic cells with the ability to adopt a spectrum of functional states. Anti-tumor macrophages (commonly known as classically activated macrophages or M1-like macrophages) are capable of anti-tumor functions such as phagocytosis, cellular cytotoxicity, and antigen presentation to orchestrate an adaptive immune response. Pro-tumor macrophages (commonly known as alternatively activated macrophages or M2-like macrophages) are potent players in tumor-supporting processes such as angiogenesis and immunosuppression. It is known that signals from the solid tumor microenvironment generally lead to macrophage polarization to the pro-tumor phenotype. Therefore, methods to maintain the anti-tumor phenotype of macrophages or to prevent their re-programming toward the pro-tumor phenotype represent advancement in the field of cancer therapy.

It has now been found, in accordance with the present invention, that the cytokine, Interleukin-31 (IL-31), is capable of maintaining the ex-vivo-induced anti-tumor phenotype of macrophages once the adoptively transferred macrophages enter the cancer tissue and encounter signals produced within the tumor microenvironment, thereby maintaining their anti-tumor phenotype and therapeutic potential. Il-31 is, therefore, of benefit in macrophage-based adoptive cell therapy for treatment of cancer.

In one aspect of the present invention, macrophages are genetically manipulated so as to express human IL-31 or both IL-31 and a chimeric antigen receptor (CAR).

In another aspect of the present invention, genetically unmodified macrophages or macrophages genetically-modified so as to express CAR can be administered to a cancer patient along with an infusion of IL-31.

These and other aspects of the invention will be described in more detail in the section Detailed Description of the Invention hereinafter.

BRIEF DESCRIPTION OF THE DRAWINGS

FIG. 2B shows that the rate of tumor growth is significantly lower in mice injected with IL-31-expressing J774 monocyte-macrophages (J774-NSPI-IL-31) in comparison to both control groups (control and J774-NSPI). Shown are mean values±SD (n=6 mice per treatment group), *$p<0.05$.

FIG. 3A: Tumor volume was monitored over time. Data are presented as mean±S.D; n=6 mice per group. *$p<0.001$. FIG. 3B: Kaplan-Meier survival analysis.

DETAILED DESCRIPTION OF THE INVENTION

Figure 1:
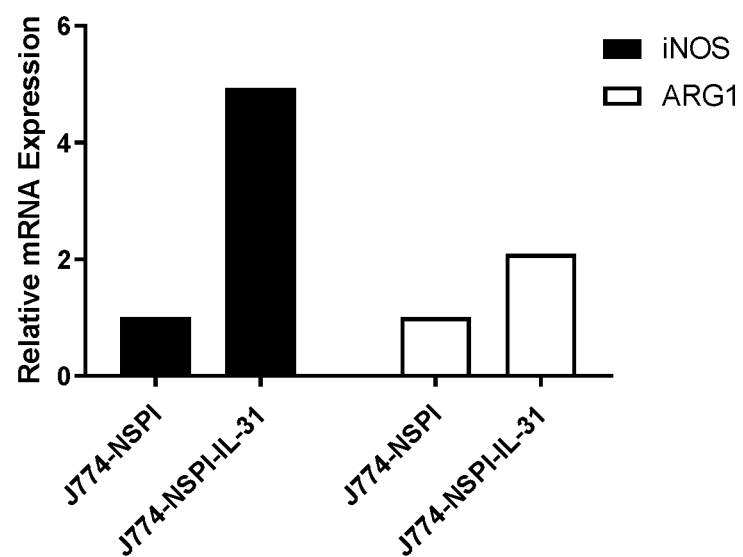
FIG. 1 shows the relative expression levels of arginase 1 (ARG1) and inducible nitric oxide synthase (iNOS) in control and IL-31-expressing J774 cells. The monocyte-macrophage cell line, J774, was genetically modified to constitutively overexpress IL-31 using a lentiviral transduction system. Control cells transduced with empty vector are referred to as J774-NSPI. Cells transduced with the IL-31-encoding vector are referred to as J774-NSPI-IL-31. Total RNA was extracted from J774-NSPI and J774-NSPI-IL-31 cells. Real-time PCR was performed to evaluate relative expression levels of the enzymes, arginase 1 (ARG1) and inducible nitric oxide synthase (iNOS). Expression levels were normalized to Hsp90.

Before describing the products and methods of the invention, it should be understood that this invention is not limited to the particular methodology and protocols as described herein. It is also to be understood that the terminology used herein is for the purpose of describing particular embodiments of the invention only and, if not defined otherwise, it is not intended to limit the scope of the present invention which will be recited in the appended claims.

It must also be noted that as used herein and in the appended claims, the singular forms "a", "an", and "the" include plural reference unless the context clearly dictates otherwise.

For better understanding of the invention, several terms used in the present application will be defined herein.

The term "tumor" herein referenced also as "cancer" refers to an abnormal growth of tissue. The present invention is directed to treatment of solid primary or metastatic malignant tumors. The term "anti-tumor effect" as used herein refers to preventing, inhibiting or stopping the formation or growth of tumors.

The term "monocyte" refers to a type of leukocyte found in the blood stream that, upon entering a tissue, differentiates into a macrophage or dendritic cell. Monocytes are the largest type of white blood cells and play an important role in the adaptive immunity process.

Monocytes typically circulate through the blood for 1-3 days before migrating into tissues, where they become macrophages or dendritic cells.

The term "macrophage" refers to a large white blood cell that is an important part of our immune system. It is a tissue-resident professional phagocyte and antigen-presenting cell with the ability to adopt a spectrum of functional states in response to environmental or external signals. Macrophages either originate from circulating monocytes that have migrated from the bloodstream into any tissue in the body, where they aid in phagocytosis to eliminate harmful materials such as foreign substances, cellular debris and cancer cells. Macrophages may be also established independently of monocytes during fetal development.

Macrophages exist in a variety of phenotypes which are determined by the role they play in wound maturation. The term "naïve macrophage" as used herein refers to a macrophage that has not been stimulated by environmental or external signals. Naïve macrophages, commonly known as M0 macrophages, have an uncommitted (or unpolarized) phenotype.

The term "anti-tumor macrophage" as used herein, refers to an activated macrophage capable of anti-tumor activities such as phagocytosis, cellular cytotoxicity, antigen presentation and cytokine secretion. Anti-tumor macrophages exist in a continuum of activation states. At the extreme of the continuum are macrophages commonly known as 'classically activated macrophages' or M1 macrophages. Anti-tumor macrophages are characterized by the upregulation of at least one surface marker selected from, but not limited to, CD40, CD68, CD80, CD86, HLA-DR, IL1R, SOCS3, TLR2, TLR4, PDL1 and the downregulation of at least one surface marker selected from, but not limited to, CD206 and CD163.

The term "pro-tumor macrophage" as used herein refers to an activated macrophage capable of tumor-supporting activities such as angiogenesis and immunosuppression. Pro-tumor macrophages exist in a continuum of activation states. At the extreme of the continuum are macrophages commonly known as 'alternatively activated macrophages' or M2 macrophages. Pro-tumor macrophages are characterized by the upregulation of at least one surface marker selected from, but not limited to, CD206 and CD163, and the downregulation of at least one surface marker selected from, but not limited to, CD40, CD68, CD80, CD86, HLA-DR, IL1R, SOCS3, TLR2, TLR4, PDL 1.

The term "macrophage-based adoptive cell therapy" as used herein, refers to a type of adoptive cell therapy in which autologous or allogeneic macrophages are administered to a subject for a therapeutic purpose. "Autologous" refers to any material derived from the same individual to whom it is later to be re-introduced. "Allogeneic" refers to any material derived from a different individual of the same species.

In accordance with the present invention, the cytokine IL-31 is used in combination with macrophage-based adoptive cell therapy wherein the presence of IL-31 serves to maintain and/or enhance the anti-tumor effect of the administered cells.

In a first aspect, the present invention is directed to macrophages which are genetically modified to express (i) human IL-31 of the sequence as set forth in SEQ ID No. 1 or peptide which is at least about 70% homologous to the IL-31 sequence as set forth in SEQ ID No.1; or (ii) a fused protein comprising human IL-31 of the sequence as set forth in SEQ ID No. 1 or peptide which is at least about 70% homologous to the IL-31 sequence as set forth in SEQ ID No.1, wherein in the fused protein the human IL-31 or peptide is attached to an immunoglobulin amino acid sequence comprising IgG.

As used herein, whenever human IL-31 is mentioned the reference is to the protein having the sequence set forth in SEQ ID No. 1.

In one preferred embodiment, the macrophages of the invention are genetically modified to express human IL-31.

In some embodiments, the macrophages are genetically modified to express a peptide which is at least about 70% homologous to the IL-31 sequence as set forth in SEQ ID No.1. In some other embodiments, the macrophages are genetically modified to express a fused protein wherein the IL-31 or the peptide is attached to an immunoglobulin amino acid sequence comprising IgG.

For preparation of genetically-modified macrophages, genetic modification is preferably achieved by introducing nucleic acid sequences (DNA or RNA) into a population of cells (monocytes, naïve macrophages or anti-tumor macrophages) by viral transduction methods. To do this, the polynucleotide of interest is first inserted into a viral expression plasmid by molecular cloning techniques well-known in the art (described in Sambrook et al., 2012) Viral expression plasmids encode a viral genome or parts thereof, based on the genomes of viruses. Lentiviral plasmids are preferred as they allow stable integration of the polynucleotide of interest into the genome of dividing and non-dividing target cells. Lentiviral expression plasmids are typically used in conjunction with lentiviral packaging and envelope plasmids to produce infectious viral particles (virions). The virions are then used to transduce target cells in a process known as lentiviral transduction, thereby introducing the polynucleotide or polynucleotides of interest to a population of the target cells.

In one embodiment of the invention, for preparation of the macrophages genetically-modified to express human IL-31 of the amino acid sequence as set forth in SEQ ID No. 1 (shown in WO 2015/173812), the nucleic acid sequence as set forth in SEQ ID No. 2 (shown in WO 2015/173812) that encodes human IL-31, is introduced into a population of cells selected from monocytes, naïve macrophages or anti-tumor macrophages by lentiviral transduction methods.

The monocytes or macrophages used for the genetic modification are obtained from a subject, preferably a human donor. The donor may be the same subject to whom the genetically-modified macrophages are later to be re-introduced (i.e., a donor of autologous cells) or an HLA-matched donor (i.e., a donor of allogeneic cells). The cells can be isolated from a number of sources, including peripheral blood, bone marrow, lymph node tissue, spleen tissue, umbilical cord, ascites fluid and tumors. Preferably, peripheral blood is collected from a human subject. The preferred method for isolating monocytes from peripheral blood samples comprises techniques known in the art such as leukapheresis followed by elutriation. The isolated monocytes may be propagated in culture using methods familiar to those skilled in the art. The monocytes may be differentiated into naïve macrophages by culturing the monocytes for 4 to 8 days in the presence of growth factors, such as GM-CSF, that stimulate the differentiation of monocytes to macrophages (Andreesen et al., 1990). The naïve macrophages may be activated into anti-tumor macrophages according to the known in the art "macrophage activated killer" or "MAK" protocol, wherein macrophages are stimulated with activating agents selected from, but not limited to, interferon-gamma (IFN-γ), muramyl tripeptide phosphatidylethanolamine (MTP-PE), mifamurtide and lipopolysaccharide (LPS) (Lee et al., 2016). This stimulation is performed for 18 hours prior to administration of the anti-tumor macrophages to the subject. The MAK protocol typically yields up to $10^9$ anti-tumor macrophages per subject on a weekly basis.

The invention is further directed to a pharmaceutical composition comprising the macrophages which are genetically modified to express (i) human IL-31 of the sequence as set forth in SEQ ID No. 1 or peptide which is at least about 70% homologous to the IL-31 sequence as set forth in SEQ ID No.1; or (ii) a fused protein comprising human IL-31 of the sequence as set forth in SEQ ID No. 1 or peptide which is at least about 70% homologous to the IL-31 sequence as set forth in SEQ ID No.1, wherein in the fused protein the human IL-31 or peptide is attached to an immunoglobulin amino acid sequence comprising IgG, and a pharmaceutically acceptable carrier. In some embodiments, the pharmaceutical composition comprises macrophages which are genetically modified to express human IL-31.

The pharmaceutical composition above is intended for use in the treatment of cancer.

In this aspect, the present invention further relates to a method for treating cancer comprising administering to a patient in need a therapeutically effective amount of macrophages which are genetically modified to express (i) human IL-31 of the sequence as set forth in SEQ ID No. 1 or peptide which is at least about 70% homologous to the IL-31 sequence as set forth in SEQ ID No.1; or (ii) a fused protein comprising human IL-31 of the sequence as set forth in SEQ ID No. 1 or peptide which is at least about 70% homologous to the IL-31 sequence as set forth in SEQ ID No.1, wherein in the fused protein the human IL-31 or peptide is attached to an immunoglobulin amino acid sequence comprising IgG.

In a second aspect, the present invention is directed to a method for treating cancer comprising administering to a patient in need a therapeutically effective amount of genetically unmodified macrophages along with an infusion of: (i) human IL-31 of the sequence as set forth in SEQ ID N. 1 or peptide which is at least about 70% homologous to the IL-31 sequence as set forth in SEQ ID No.1; (ii) a fused protein comprising human IL-31 of the sequence as set forth in SEQ ID No. 1 or peptide which is at least about 70% homologous to the IL-31 sequence as set forth in SEQ ID No.1, wherein in the fused protein the human IL-31 or peptide is attached to an immunoglobulin amino acid sequence comprising IgG: or (iii) a complex comprising human IL-31 or a fused protein comprising human IL-31 of the sequence as set forth in SEQ ID No. 1 or peptide which is at least about 70% homologous to the IL-31 sequence as set forth in SEQ ID No.1 and a non-proteinaceous or proteinaceous moiety selected from polyethylene glycol (PEG), polyvinyl pyrrolidone (PVP), divinyl ether, albumin, maleic anhydride copolymer (DIVEMA), polysialic acid (PSA), poly (styrene comaleic anhydride) (SMA), hyaluronic acid (HA), alginic acid (AA), polyhydroxyethyl methacrylate (Poly-HEMA), glyme or polyisopropylacrylamide.

The human IL-31 of the SEQ ID No. 1, the peptide, the fused protein and the complex mentioned above are described in WO 2015/173812herein incorporated by reference as fully disclosed herein.

In some embodiments, fused proteins are used that comprise IL-31 together with one or more molecules described above that extend the half-life of IL-31 in the plasma, stabilize IL-31 or protect it in the blood stream or at the tissue. In some embodiments, the fused protein comprises IL-31 attached to a heterologous amino acid sequence that may comprise a immunoglobulin amino acid sequence. In some embodiments, the fused protein comprises IL-31 and IgG of any class, e.g., IgG1, IgG2, IgG3. In some embodiments, the two protein moieties are separated by a linker, e.g., of 4-12 amino acids, which form a cleavage site for enzymes.

In some embodiments, a complex is used comprising human IL-31 or a fused protein comprising human IL-31 of the sequence as set forth in SEQ ID No. 1 or peptide which is at least about 70% homologous to the IL-31 sequence as set forth in SEQ ID No.1 and a non-proteinaceous or proteinaceous moiety as specified above. The complex may be in the form of a liposome or a micelle.

In a third aspect, the present invention relates to macrophages which are genetically modified to express a chimeric antigen receptor (CAR) (herein CAR macrophages) that is designed to be expressed in an immune effector cell, such that the macrophages expressing the CAR possess targeted effector activity including phagocytosis, targeted cellular cytotoxicity, antigen presentation and cytokine secretion.

In some embodiments, the CAR comprises an extracellular antigen-binding domain that binds to an antigen on a target cell to which the targeted effector activity is directed, a transmembrane domain, and an intracellular domain.

The antigen binding domain binds to an antigen on a target cell, thereby directing the targeted effector activity against a cell expressing a specific antigen. For example, the antigen is a tumor antigen that is specific for a tumor or cancer of interest. The antigen binding domain can include any domain that binds to the antigen and may include, but is not limited to, a monoclonal antibody, a polyclonal antibody, a synthetic antibody, a human antibody, a humanized antibody, a non-human antibody, and any fragment thereof. In some embodiments, the extracellular antigen-binding domain of the CAR is a single chain variable fragment (scFv) derived from an antibody against an antigen including CD19, CD22, or HER2.

The transmembrane domain of the CAR connects the antigen binding domain to the intracellular domain. The transmembrane domain may be derived either from a natural source such as the transmembrane region of any membrane bound or transmembrane protein, or from a synthetic source in which case it will comprise predominantly hydrophobic residues. In some embodiments, the CAR includes the transmembrane domain of CD8, CD28 or of CD3.

The intracellular domain of the CAR represents the cytoplasmic portion of the CAR and is responsible for the activation of the macrophages in which the CAR is expressed. The intracellular domain of the CAR can be the cytoplasmic portion of a surface receptor, a stimulatory or co-stimulatory molecule, or a molecule that initiates signal transduction in the macrophage, such molecules including the intracellular domain of Megf10 (multiple epidermal growth factor-like domains protein 10), FcRγ (the common subunit of Fc receptors), CD3ζ, or of Dectin-1.

To generate genetically modified macrophages that express a CAR, a nucleic acid sequence encoding a recombinant receptor is introduced to the population of cells by lentiviral transduction as described above, wherein the recombinant receptor comprises an antigen binding domain, a transmembrane domain and an intracellular domain.

In accordance with this aspect, a method for treating cancer is provided comprising administering to a patient in need a therapeutically effective amount of CAR macrophages as defined above along with an infusion of: (i) human IL-31 of the sequence as set forth in SEQ ID N. 1 or peptide which is at least about 70% homologous to the IL-31 sequence as set forth in SEQ ID No.1; (ii) a fused protein comprising human IL-31 of the sequence as set forth in SEQ ID No. 1 or peptide which is at least about 70% homologous to the IL-31 sequence as set forth in SEQ ID No.1, wherein in the fused protein the human IL-31 or peptide is attached to an immunoglobulin amino acid sequence comprising IgG: or (iii) a complex comprising human IL-31 or a fused protein comprising human IL-31 of the sequence as set forth in SEQ ID No. 1 or peptide which is at least about 70% homologous to the IL-31 sequence as set forth in SEQ ID No.1 and a non-proteinaceous or proteinaceous moiety selected from polyethylene glycol (PEG), polyvinyl pyrrolidone (PVP), divinyl ether, albumin, maleic anhydride copolymer (DI-VEMA), polysialic acid (PSA), poly (styrene comaleic anhydride) (SMA), hyaluronic acid (HA), alginic acid (AA), polyhydroxyethyl methacrylate (Poly-HEMA), glyme or polyisopropylacrylamide.

In a fourth aspect, the invention is directed to macrophages which are genetically modified to express both: (i) human IL-31 of the sequence as set forth in SEQ ID No. 1 or peptide which is at least about 70% homologous to the IL-31 sequence as set forth in SEQ ID No.1 or a fused protein comprising human IL-31 of the sequence as set forth in SEQ ID No. 1 or peptide which is at least about 70% homologous to the IL-31 sequence as set forth in SEQ ID No.1, wherein in the fused protein the human IL-31 or peptide is attached to an immunoglobulin amino acid sequence comprising IgG; and (ii) a chimeric antigen receptor (CAR) that is designed to be expressed in immune effector cells, such that the macrophages expressing the CAR possess targeted effector activity, and wherein the CAR comprises an extracellular antigen-binding domain, a transmembrane domain and an intracellular domain, these domains being as previously described above.

The preparation of genetically-modified macrophages that express both a CAR and IL-31 as defined in the above paragraph is achieved by inserting both a nucleic acid sequence encoding the IL-31 protein, peptide or fused protein as defined in (i) and a nucleic acid sequence encoding the CAR (ii) into a lentiviral vector plasmid by molecular cloning techniques well-known in the art (described in Sambrook et al.) and transducing into a population of cells (monocytes, naïve macrophages or anti-tumor macrophages) by lentiviral transduction methods as known in the art. Expression of the two polynucleotides may be driven by two independent promoters. Alternatively, the two polynucleotides of interest may be fused in frame such that the sequence encoding the intracellular domain of the CAR is followed by a sequence encoding a 2A self-cleavage peptide followed by a sequence encoding the IL-31 protein or peptide. In another alternative, the population of cells can be transduced with two lentivirus transduction vectors, wherein one vector comprises the nucleic acid sequence coding for (i) and the other vector codes for the CAR polypeptide (ii).

According to this aspect, the invention provides pharmaceutical compositions comprising macrophages which are genetically modified to express both: (i) human IL-31, the peptide or the fused protein as described above and (ii) the CAR polypeptide as described above, and a pharmaceutically acceptable carrier. These pharmaceutical compositions are for use in treatment of cancer.

The pharmaceutical compositions of the present invention comprise the cells—unmodified macrophages or genetically-modified macrophages, or the human IL-31 protein, the peptide at least 70% homologous to the SEQ ID No.1 or IL-31 fused proteins, and pharmaceutically acceptable carriers, diluents or excipients. They may be manufactured by methods well-known in the art, for example as described in Remington's Pharmaceutical Sciences, Mack Publishing Co., Easton, Pa., latest edition, which is incorporated herein by reference.

The pharmaceutical compositions comprising may be administered to the patients by various suitable routes such as intravenously, intraperitoneally and intratumorally. In preferred embodiments, the composition is administered intravenously. The amount and frequency of administration will be determined by the medical doctor responsible for the patient's treatment and will depend on the type and severity of the patient's disease, and his age and condition. Examples of therapeutic dosages of cells include weekly doses of $10^7$ to $10^9$ cells (macrophages) per dose for a period of up to 8 weeks. When the IL-31 is administered along with genetically unmodified macrophages or with CAR-macrophages, the macrophages are administered once or each 2-3 weeks, and the IL-31 is administered continuously (daily).

The cancer to be treated according to the present invention may be a primary or a metastatic solid tumor including bladder, brain, breast, cervical, colon, colorectal, glioblastoma, head and neck, kidney, liver, lung, melanoma, ovarian, pancreas, pituitary, prostate, rectal, sarcoma tumors, skin, stomach, testicular, thyroid and uterine cancer.

The invention will now be illustrated by the following non-limiting Examples.

EXAMPLES

Materials and Methods
i) Cell Culture

The murine monocyte-macrophage J774, murine 4T1 breast carcinoma, murine EMT6 breast carcinoma and human 293T cell lines were purchased from the American Type Culture Collection (ATCC, USA). The cells were passaged in culture for no more than 4 months after being thawed from authentic stocks. All cells were tested to be negative for *mycoplasma*. Cells were cultured in Dulbecco's modified eagle medium (DMEM, Sigma-Aldrich) supplemented with 10% fetal bovine serum (FBS), 1% L-glutamine, 1% sodium-pyruvate and 1% penicillin-streptomycin (all purchased from Biological Industries) at 37° C. in 5% $CO_2$.

ii) Lentiviral Production

A PCR-amplified fragment encoding murine IL-31 was cloned between BamHI and XhoI sites within the multiple cloning site of the NSPI-CMV-Myc-His lentiviral vector (Addgene) to generate the NSPI-CMV-IL-31-Myc-His construct. Lentiviruses were generated by calcium phosphate transient transfection of 293T cells ($1.2 \times 10^6$ cells seeded in a 10 cm culture dish) with a three-plasmid combination as follows: 15 μg lentiviral vector (i.e., either NSPI-CMV-Myc-His empty control vector, or NSPI-CMV-IL-31-Myc-His); 10 μg packaging plasmid δNRF; 5 μg envelope plasmid VSV-G. Packaging and envelope plasmids were purchased from Abm. Culture medium was collected 96 hours following transfection, filtered and supplemented with polybrene (8 μg/ml, final concentration). Culture medium containing live virus was used immediately for the infection of J774 cells, as described in the section "Lentiviral transduction".

iii) Lentiviral Transduction

J774 cells were seeded in 6-well culture plates at a density of $6 \times 10^5$ cells/well. The cells were infected the following day by replacing the culture medium with virus-containing medium. Plates were centrifuged at 1100 g for 1.5 h at 32° C. The infection procedure was repeated the following day with a fresh lentiviral production. Transduced cells were selected over 10 days by culturing in medium supplemented with 4 μg/ml puromycin. Control cells transduced with empty vector are referred to as J774-NSPI. Cells transduced with the IL-31-encoding vector are referred to as J774-NSPI-IL-31.

iv) Real-Time PCR

Total RNA was extracted from J774-NSPI and J774-NSPI-IL-31 cells using an RNA purification kit (Norgen Biotek). RNA was reverse transcribed to cDNA using a high capacity cDNA reverse transcription kit (Applied Biosystems). Real-time PCR was performed to evaluate relative expression levels of the enzymes, arginase 1 (ARG1) and inducible nitric oxide synthase (iNOS). Expression levels were normalized to Hsp90. For ARG1, the primers were CTCCAAGCCAAAGTCCTTAGAG (SEQ ID No. 3) and AGGAGCTGTCATTAGGGACATC (SEQ ID No. 4). For iNOS, the primers were GTTCTCAGCCCAACAATA-CAAGA (SEQ ID No. 5) and GTGGACGGGTCGATGT-CAC (SEQ ID No. 6). For Hsp90, the primers were TCGTCAGAGCTGATGATGAAGT (SEQ ID No. 7) and GCGTTTAACCCATCCAACTGAAT (SEQ ID No. 8). All samples were assayed in triplicate and analyzed using the AACT method to assess relative fold change in ARG1 and iNOS expression levels.

v) Peritoneal Macrophage Isolation

Female BALB/c mice, 8 weeks of age (Harlan, Israel), were intraperitoneally injected with 3 ml 4% thioglycollate (wt/vol in saline; Sigma-Aldrich) to elicit large numbers of macrophages in the peritoneal cavity. After 48 hours, mice were intraperitoneally injected with $2 \times 10^6$ EMT6 breast carcinoma cells which had been pre-irradiated with 60Gy. This step serves to expose macrophages to tumor antigens in vivo. Mice were sacrificed 24 hours later and peritoneal macrophages were collected as follows. Ice-cold PBS (5 ml) was injected into the peritoneal cavity. The fluid was withdrawn and centrifuged at 350 g for 5 min at 4° C. to sediment cells. The cell pellet was resuspended in 10 ml RBC lysis buffer (Sigma-Aldrich) and incubated for 10 min at room temperature in order to lyse red blood cells. The cell solution was recentrifuged at 350 g for 5 min at 4° C., and the cell pellet was resuspended in serum-free RPMI-1640 medium (Sigma-Aldrich). The peritoneal exudate cells were seeded into 10 cm culture dishes and incubated at 37° C. for approximately 2 hours to allow cells to adhere. Non-adherent cells were removed by extensive washing with PBS. The remaining adherent peritoneal cells (which represent macrophages) were cultured overnight in RPMI-1640 medium (Sigma-Aldrich) containing 10% FBS (Biological Industries) prior to polarization treatments (which are described in the section, "Macrophage polarization ex vivo").

vi) Macrophage Polarization Ex Vivo

Cultured peritoneal macrophages were treated with 20 ng/ml IL-4 and 100 ng/ml IL-31 murine recombinant proteins (both from Peprotech) for 48 hours. IL-4 treatment serves to polarize the macrophages toward the pro-tumor M2-like phenotype (Mantovani and Locati, 2013). Co-treatment with IL-31 is performed to test the ability of IL-31 to polarize the macrophages from a pro-tumor into an anti-tumor phenotype. Macrophages treated according to this protocol (i.e., macrophages co-treated with IL-4 and IL-31) are hereafter referred to as IL-31-educated macrophages. The IL-31-educated macrophages were detached by digestion with accutase (Sigma-Aldrich), washed in PBS, resuspended in serum-free RPMI medium, and counted with a hemocytometer. Typically, $\sim 5 \times 10^5$ IL-31-educated macrophages were obtained from $\sim 1 \times 10^7$ peritoneal exudate cells per mouse.

vii) Tumor Models and Treatment Protocols

Adoptive transfer model using the monocyte-macrophage cell line J774: Murine 4T1 breast carcinoma cells ($5 \times 10^5$) were orthotopically implanted into the mammary fat pad of 8-week old female BALB/c mice (Harlan, Israel). Tumor size was assessed regularly with Vernier calipers using the formula width$^2 \times$length$\times 0.5$. When tumors reached an average size of 75 mm$^3$, mice were randomly assigned to 3 treatment groups: i) mice were left untreated; ii) mice received a single intravenous injection (through the tail vein) of $2 \times 10^6$ control J774-NSPI cells; iii) mice received a single intravenous injection (through the tail vein) of $2 \times 10^6$ J774-NSPI-IL-31 cells; n=6 mice per group. Tumor growth was assessed regularly. When tumors reached a size of ~1000 mm$^3$, mice were sacrificed.

Adoptive transfer model using IL-31-educated macrophages: Murine EMT6 breast carcinoma cells ($5 \times 10^5$ cells) were orthotopically implanted into the mammary fat pad of BALB/c female mice, 8 weeks of age (Harlan, Israel). Seven days after implantation, when tumors reached an average size of 100 mm$^3$, IL-31-educated macrophages were injected into the retro-orbital sinus ($5 \times 10^5$ cells in a volume of 150 μl RPMI per dose). Thereafter, mice received weekly boosts of macrophage injections (0.3-1.5$\times 10^6$ cells in a volume of 150 μl RPMI per dose). Control mice were not injected with macrophages; n=6 mice per group. Tumor volume was monitored by caliper measurements according to the formula width$^2 \times$length$\times 0.5$. Mice were sacrificed at endpoint (when tumors reached a size of 1500 mm$^3$).

viii) ELISA

Blood was collected from mice on day 19 after 4T1 tumor cell implantation. Briefly, the submandibular vein was punctured with a needle, and 100-150 μl blood was collected into EDTA-containing tubes. Blood samples were centrifuged at 2000 g for 15 min and the supernatant (plasma) was collected. The level of IL-31 in plasma was determined using a mouse IL-31 platinum ELISA kit (Invitrogen).

ix) Statistical Analysis

Data is expressed as mean±standard deviation (SD). Statistical significance of differences was assessed by multiple t test. Differences were considered significant at p values below 0.05.

Example 1. In Vitro Characterization of a Genetically Modified Monocyte-Macrophage Cell Line Expressing IL-31

The murine monocyte-macrophage cell line, J774, was genetically modified to constitutively overexpress IL-31 using a lentiviral transduction system. To determine whether IL-31 expression affects macrophage polarization, we evaluated the expression levels of the arginine metabolizing enzymes, iNOS (which is expressed by M1-like macrophages) and ARG1 (which is expressed by M2-like macrophages) in control and IL-31-expressing J774 cells using real-time PCR. FIG. 1 shows that the expression level of iNOS is increased by 5-fold in IL-31-expressing cells in comparison to control, whereas the expression level of ARG1 is increased by only 2-fold in IL-31-expressing cells in comparison to control. This suggests that IL-31 polarizes the macrophages predominantly toward an M1-like phenotype.

Figure 2A:
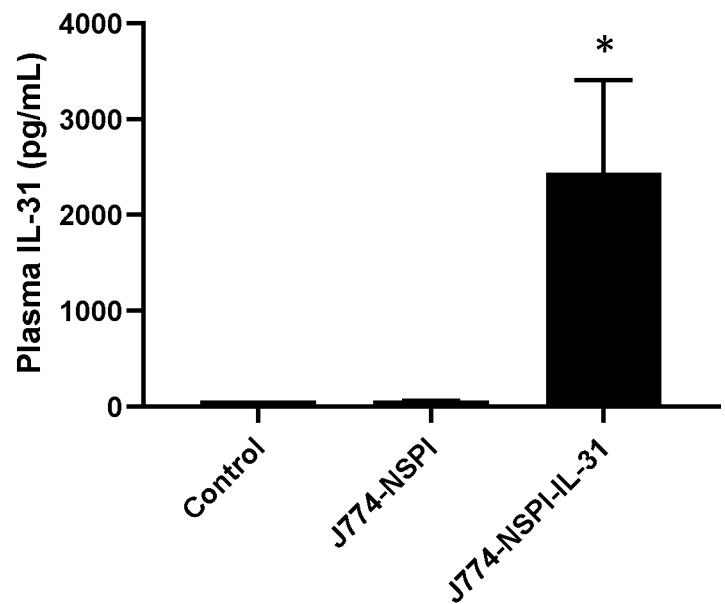
FIGS. 2A & 2B show the therapeutic effect of adoptively transferred monocyte-macrophages expressing IL-31 in a primary breast tumor model. Murine 4T1 breast carcinoma cells were orthotopically implanted into the mammary fat pad of BALB/c mice. When the tumors reached an average size of 75 mm$^3$, mice were either left untreated (control), or they received a single intravenous injection of control monocyte-macrophages (J774-NSPI) or IL-31-expressing monocyte-macrophages (J774-NSPI-IL-31). On day 19, blood samples were collected from the submandibular vein and plasma was prepared. The level of IL-31 in plasma was determined by ELISA (FIG. 2A). Tumor volume was measured regularly throughout the experiment.
Figure 2B:
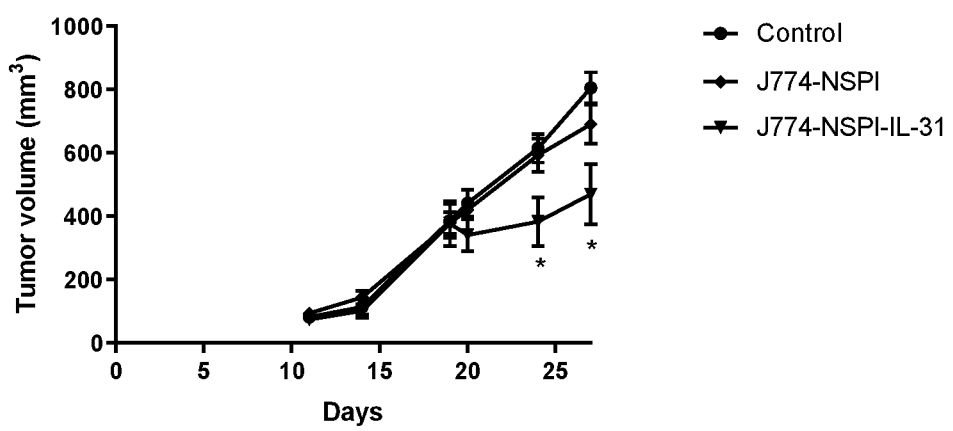

Example 2. Adoptive Transfer of Monocyte-Macrophage Cells Expressing IL-31 Inhibits Tumor Growth in a Murine Breast Carcinoma Model A murine 4T1 primary breast carcinoma model was employed to determine the therapeutic potential of adoptively transferred monocyte-macrophage cells expressing IL-31. Briefly, murine 4T1 breast carcinoma cells were orthotopically implanted into the mammary fat pad of BALB/c mice. When the tumors reached an average size of 75 mm$^3$, mice were either left untreated, or they received a single intravenous injection of control or IL-31-expressing J774 monocyte-macrophages. FIG. 2A demonstrates that mice injected with IL-31-expressing J774 monocyte-macrophages exhibit high plasma levels of IL-31 (2.4 ng/ml). The plasma level of IL-31 in control untreated mice and in mice injected with control J774 monocyte-macrophages was below the detection threshold. In addition, as expected, mice injected with IL-31-expressing J774 monocyte-macrophages exhibited signs of dermatitis, such as hair loss and scratching behavior. Tumor growth was monitored throughout the experiment, and growth rates were compared between the groups. FIG. 2B shows that the rate of tumor growth is significantly lower in mice injected with IL-31-expressing J774 monocyte-macrophages, in comparison to both control groups (i.e., untreated mice and mice injected with control J774 monocyte-macrophages). The data demonstrate the inhibitory effect of adoptively transferred monocyte-macrophages expressing IL-31 on primary tumor growth.

Example 3. Adoptive Transfer of IL-31-Educated Macrophages Inhibits Tumor Growth in a Murine Breast Carcinoma Model This is a proof of concept example to show that IL-31 enhances the anti-tumor effect of tumor educated macrophages, namely macrophages that are directed against tumor antigens.

Examples of macrophages directed against tumor antigens include: macrophages exposed to lethally irradiated tumor cells; genetically modified macrophages that express a receptor for a tumor antigen; genetically modified macrophages that express a chimeric antigen receptor (CAR) as well as macrophages that are co-cultured with antigen presenting cells (dendritic cells) from patients.

In the present Example, there is evidence of feasibility to back up this statement. In this experiment, the macrophages are exposed to lethally irradiated tumor cells in vivo, isolated and treated with IL-4. The IL-4 treatment serves to mimic the signals from a tumor that would usually turn the macrophages into pro-tumor macrophages (tumor-associated macrophages). After treatment of the macrophages with IL-31, it was found that macrophages educated for tumor antigens and IL-31 demonstrated anti-tumor activity. This emphasizes that the education of macrophages to tumor antigens (in the example it is lethally irradiated cells, but can be other ways to ensure such education e.g., CAR), along with IL31 increases anti-tumor response.

Figure 3A:
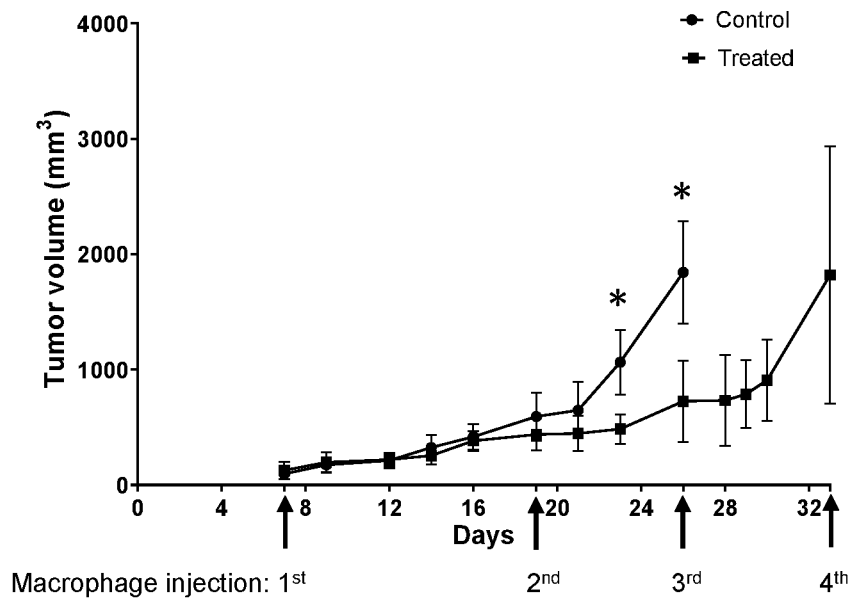
FIGS. 3A & 3B show the therapeutic effect of adoptively transferred, IL-31-educated macrophages in a primary breast tumor model. EMT6 breast carcinoma cells (5×10$^5$ cells) were orthotopically implanted into the mammary fat pad of BALB/c female mice (8 weeks of age). Seven days after implantation, IL-31-educated peritoneal macrophages were injected into the retro-orbital sinus. Thereafter, mice received weekly boosts of macrophage injections (indicated by arrows) at a dose of 5×10$^5$, 3×10$^5$, 5×10$^5$ and 1.5×10$^6$ cells in the first, second, third and fourth injection, respectively. Control mice were not injected with macrophages.
Figure 3B:
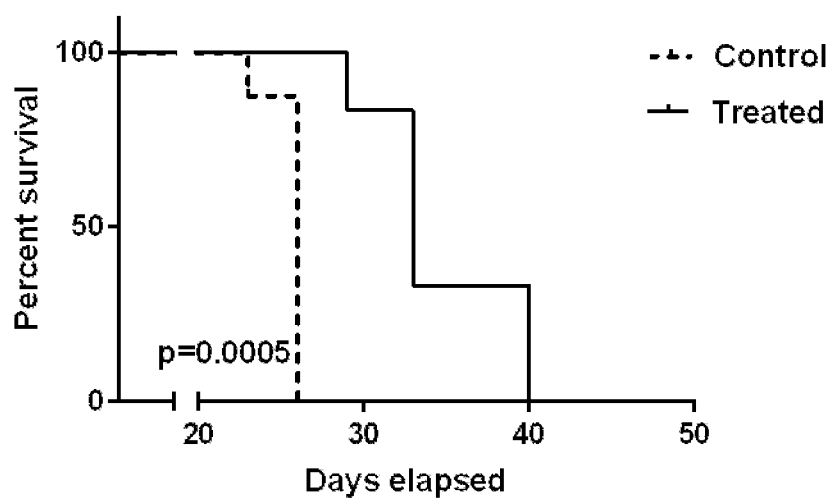

To test the ability of IL-31 to polarize macrophages from a pro-tumor into an anti-tumor phenotype, the following experiment was performed. Macrophages were harvested from the peritoneal cavity of thioglycollate-stimulated BALB/c mice. The macrophages were then treated ex vivo with a combination of IL-4 and IL-31. IL-4 treatment serves to polarize the macrophages toward the pro-tumor M2 phenotype (Mantovani and Locati, 2013). Co-treatment with IL-31 tests the ability of IL-31 to polarize the macrophages from a pro-tumor into an anti-tumor phenotype. Macrophages treated according to this protocol (i.e., macrophages co-treated with IL-4 and IL-31) are hereafter referred to as IL-31-educated macrophages. The IL-31-educated macrophages were subsequently injected into mice bearing EMT6 breast carcinoma tumors and tumor growth was monitored over time. FIG. 3A demonstrates that the rate of tumor growth was significantly reduced in mice administered with IL-31-educated macrophages in comparison to control mice that were not injected with macrophages. On day 26, tumors in macrophage-treated mice were ~3 times smaller than tumors in untreated mice. In addition, mice receiving IL-31-educated macrophages had a survival benefit of 14 days relative to untreated mice (FIG. 3B). The data demonstrate the therapeutic effect of adoptively transferred, IL-31-educated macrophages.

REFERENCES

Andreesen R, Scheibenbogen C, Brugger W, Krause S, Meerpohl H G, Leser H G, Engler H, Lohr G W: Adoptive transfer of tumor cytotoxic macrophages generated in vitro from circulating blood monocytes: a new approach to cancer immunotherapy. *Cancer research* 1990, 50(23): 7450-7456.

Beatty G L, O'Hara M: Chimeric antigen receptor-modified T cells for the treatment of solid tumors: Defining the challenges and next steps. *Pharmacol Ther* 2016, 166: 30-39.

Cornelissen C, Brans R, Czaja K, Skazik C, Marquardt Y, Zwadlo-Klarwasser G, Kim A, Bickers D R, Luscher-Firzlaff J, Luscher B et al: Ultraviolet B radiation and reactive oxygen species modulate interleukin-31 expression in T lymphocytes, monocytes and dendritic cells. *Br J Dermatol* 2011, 165(5):966-975.

Dambacher, J., Beigel, F., Seiderer, J., Haller, D., Goke, B., Auernhammer, C. J., and Brand, S. (2007). Interleukin 31 mediates MAP kinase and STAT1/3 activation in intestinal epithelial cells and its expression is upregulated in inflammatory bowel disease. Gut 56, 1257-1265.

Davidi, S., Fremder, E., Kan, T., Raviv, Z., Timaner, M., Karin, N., Hershkovitz, D., Arohneim, A., and Shaked, Y. (2017). The antiangiogenic role of the pro-inflammatory cytokine interleukin-31. Oncotarget 8, 16430-16444.

Dillon, S. R., Sprecher, C., Hammond, A., Bilsborough, J., Rosenfeld-Franklin, M., Presnell, S. R., Haugen, H. S., Maurer, M., Harder, B., Johnston, J., et al. (2004). Interleukin 31, a cytokine produced by activated T cells, induces dermatitis in mice. Nat Immunol 5, 752-760.

Ferretti, E., Tripodo, C., Pagnan, G., Guarnotta, C., Marimpietri, D., Corrias, M. V., Ribatti, D., Zupo, S., Fraternali-Orcioni, G., Ravetti, J. L., et al. (2015). The interleukin (IL)-31/IL-31R axis contributes to tumor growth in human follicular lymphoma. Leukemia 29, 958-967.

Fidler, I. J. (1974). Inhibition of pulmonary metastasis by intravenous injection of specifically activated macrophages. Cancer research 34, 1074-1078.

Fridman W H, Pages F, Sautes-Fridman C, Galon J: The immune contexture in human tumours: impact on clinical outcome. *Nat Rev Cancer* 2012, 12(4):298-306.

Harrer, D. C., Dorrie, J., and Schaft, N. (2018). Chimeric Antigen Receptors in Different Cell Types: New Vehicles Join the Race. Hum Gene Ther 29, 547-558.

Hermanns, H. M. (2015). Oncostatin M and interleukin-31: Cytokines, receptors, signal transduction and physiology. Cytokine Growth Factor Rev 26, 545-558.

Houot R, Schultz L M, Marabelle A, Kohrt H: T-cell-based Immunotherapy: Adoptive Cell Transfer and Checkpoint Inhibition. *Cancer Immunol Res* 2015, 3(10):1115-1122.

Huang Y, Li D, Qin D Y, Gou H F, Wei W, Wang Y S, Wei Y Q, Wang W: Interleukin-armed chimeric antigen receptor-modified T cells for cancer immunotherapy. *Gene Ther* 2017.

Jackson, H. J., Rafiq, S., and Brentjens, R. J. (2016). Driving CAR T-cells forward. Nature reviews Clinical oncology 13, 370-383.

Lee, S., Kivimae, S., Dolor, A., and Szoka, F. C. (2016). Macrophage-based cell therapies: The long and winding road. J Control Release 240, 527-540.

Lei, Z., Liu, G., Huang, Q., Lv, M., Zu, R., Zhang, G. M., Feng, Z. H., and Huang, B. (2008). SCF and IL-31 rather than IL-17 and BAFF are potential indicators in patients with allergic asthma. Allergy 63, 327-332.

Mantovani, A., and Locati, M. (2013). Tumor-associated macrophages as a paradigm of macrophage plasticity, diversity, and polarization: lessons and open questions. Arterioscler Thromb Vasc Biol 33, 1478-1483.

Maude S L, Frey N, Shaw P A, Aplenc R, Barrett D M, Bunin N J, Chew A, Gonzalez V E, Zheng Z, Lacey S F et al: Chimeric antigen receptor T cells for sustained remissions in leukemia. *N Engl J Med* 2014, 371(16):1507-1517.

Neis, M. M., Peters, B., Dreuw, A., Wenzel, J., Bieber, T., Mauch, C., Krieg, T., Stanzel, S., Heinrich, P. C., Merk, H. F., et al. (2006). Enhanced expression levels of IL-31 correlate with IL-4 and IL-13 in atopic and allergic contact dermatitis. J Allergy Clin Immunol 118, 930-937.

Niyonsaba F, Ushio H, Hara M, Yokoi H, Tominaga M, Takamori K, Kajiwara N, Saito H, Nagaoka I, Ogawa H et al: Antimicrobial peptides human beta-defensins and cathelicidin LL-37 induce the secretion of a pruritogenic cytokine IL-31 by human mast cells. *J Immunol* 2010, 184(7):3526-3534.

Ohmatsu, H., Sugaya, M., Suga, H., Morimura, S., Miyagaki, T., Kai, H., Kagami, S., Fujita, H., Asano, Y., Tada, Y., et al. (2012). Serum IL-31 levels are increased in patients with cutaneous T-cell lymphoma. Acta Derm Venereol 92, 282-283.

Rosenberg S A, Yang J C, Sherry R M, Kammula U S, Hughes M S, Phan G Q, Citrin D E, Restifo N P, Robbins P F, Wunderlich J R et al: Durable complete responses in heavily pretreated patients with metastatic melanoma using T-cell transfer immunotherapy. *Clinical cancer research: an official journal of the American Association for Cancer Research* 2011, 17(13):4550-4557.

Sambrook et al., 2012, Molecular Cloning: A Laboratory Manual, volumes 1-4, Cold Spring Harbor Press, NY.

Wang, B. S., Lumanglas, A. L., and Dun, F. E. (1986). Immunotherapy of a murine lymphoma by adoptive transfer of syngeneic macrophages activated with bisantrene. Cancer research 46, 503-506.

Zeng, X., Zhang, Z., Gao, Q. Q., Wang, Y. Y., Yu, X. Z., Zhou, B., and Xi, M. R. (2016). Clinical Significance of Serum Interleukin-31 and Interleukin-33 Levels in Patients of Endometrial Cancer: A Case Control Study. Dis Markers 2016, 9262919.

The invention claimed is:

1. A macrophage which is genetically modified to express (i) human IL-31 of the sequence as set forth in SEQ ID No. 1 or a peptide which is at least 85% identical to the IL-31 sequence as set forth in SEQ ID No. 1 and which binds to IL-31 receptor alpha (IL-31RA); or (ii) a fused protein comprising human IL-31 of the sequence as set forth in SEQ ID No. 1 or a peptide which is at least 85% identical to the IL-31 sequence as set forth in SEQ ID No. 1 and which binds to IL-31RA, wherein in the fused protein the human IL-31 or peptide is attached to an immunoglobulin amino acid sequence comprising IgG.

2. The macrophages according to claim 1, which is genetically modified to express human IL-31 of the sequence as set forth in SEQ ID No. 1.

3. A method of preparing genetically-modified macrophages according to claim 1, comprising introducing a nucleic acid sequence encoding human IL-31, a peptide which is at least 85% homologous identical to the IL-31 sequence as set forth in SEQ ID No. 1 and which binds to IL-31RA, or the fused protein wherein the IL-31 or the peptide is attached to an immunoglobulin amino acid sequence comprising IgG, into a population of cells selected from monocytes, naïve macrophages or anti-tumor macrophages by transduction methods.

4. The method according to claim 3, wherein the nucleic acid sequence encoding human IL-31 of the sequence as set forth in SEQ ID No. 1 is introduced into the cells by lentiviral transduction.

5. A pharmaceutical composition comprising genetically-modified macrophages according to claim 1, and a pharmaceutically acceptable carrier.

6. The pharmaceutical composition according to claim 5, wherein the macrophages are genetically modified to express human IL-31 of the sequence set forth in SEQ ID No. 1.

7. A method for treating cancer comprising administering to a patient in need thereof a therapeutically effective amount of the genetically modified macrophages according to claim 1.

8. A method for treating cancer comprising administering to a patient in need thereof a therapeutically effective amount of the pharmaceutical composition according to claim 5.

9. A macrophages which is genetically modified to express both: (i) human IL-31 of the sequence as set forth in SEQ ID No. 1 or peptide which is at least 85% identical to the IL-31 sequence as set forth in SEQ ID No. 1 and which binds to IL-31RA or a fused protein comprising human IL-31 of the sequence as set forth in SEQ ID No. 1 or peptide which is at least 85% identical to the IL-31 sequence as set forth in SEQ ID No. 1 and which binds IL-31RA, wherein in the fused protein the human IL-31 or the peptide is attached to an immunoglobulin amino acid sequence comprising IgG; and (ii) a chimeric antigen receptor (CAR) that is designed to be expressed in immune effector cells, such that the macrophages expressing the CAR possess targeted effector activity, and wherein the CAR comprises an extracellular antigen-binding domain, a transmembrane domain and an intracellular domain.

10. A pharmaceutical composition comprising macrophages according to claim 9 and a pharmaceutically acceptable carrier.

11. A method for treating cancer comprising administering to a patient in need thereof a therapeutically effective amount of the pharmaceutical composition according to claim 10.

12. The method according to claim 8, wherein the cancer is a primary or a metastatic solid tumor including bladder, brain, breast, cervical, colon, colorectal, glioblastoma, head and neck, kidney, liver, lung, melanoma, ovarian, pancreas, pituitary, prostate, rectal, sarcoma tumors, skin, stomach, testicular, thyroid and uterine cancer.

13. The macrophage according to claim 1, which is genetically modified to express a peptide which is at least 95% identical to the IL-31 sequence as set forth in SEQ ID No. 1 and which binds to IL-31RA or a fused protein comprising a peptide which is at least 95% identical to the IL-31 sequence as set forth in SEQ ID No. 1 and which binds to IL-31RA.

14. The macrophage according to claim 1, wherein the peptide which is at least 85% identical to the IL-31 sequence as set forth in SEQ ID No. 1 and which binds to IL-31RA and induces signal transduction through the IL-31RA.

15. The method according to claim 3, wherein the nucleic acid sequence encodes a peptide which is at least 95% identical to the IL-31 sequence as set forth in SEQ ID No. 1 and which binds to IL-31RA or a fused protein comprising a peptide which is at least 95% identical to the IL-31 sequence as set forth in SEQ ID No. 1 and which binds to IL-31RA.

* * * * *